United States Patent
Bujas et al.

(10) Patent No.: US 6,804,989 B2
(45) Date of Patent: Oct. 19, 2004

(54) METHOD AND APPARATUS FOR MEASURING ULTRALOW WATER PERMEATION

(75) Inventors: Roko S. Bujas, Leucadia, CA (US); Ralf Dunkel, San Diego, CA (US)

(73) Assignee: General Atomics, San Diego, CA (US)

(*) Notice: Subject to any disclaimer, the term of this patent is extended or adjusted under 35 U.S.C. 154(b) by 0 days.

(21) Appl. No.: 10/286,102

(22) Filed: Oct. 31, 2002

(65) Prior Publication Data

US 2004/0083796 A1 May 6, 2004

(51) Int. Cl.⁷ .............................................. G01N 15/08
(52) U.S. Cl. ................. 73/38; 73/38; 73/159; 73/73; 73/76
(58) Field of Search .............................. 73/38, 159, 73, 73/76

(56) References Cited

U.S. PATENT DOCUMENTS

| | | | |
|---|---|---|---|
| 3,286,509 A | * 11/1966 | Gluckman et al. | 73/38 |
| 3,580,067 A | * 5/1971 | Mandrell et al. | 73/159 |
| 3,590,634 A | * 7/1971 | Pasternak et al. | 73/38 |
| 3,937,649 A | * 2/1976 | Ridgely | 376/310 |
| 3,999,066 A | * 12/1976 | Osborne et al. | 250/304 |
| 4,656,865 A | * 4/1987 | Callan | 73/38 |
| 4,663,969 A | * 5/1987 | Bibby et al. | 73/159 |
| 4,965,450 A | * 10/1990 | Schiltz et al. | 73/76 |
| 5,159,829 A | 11/1992 | Mayer et al. | 73/38 |
| 5,390,539 A | * 2/1995 | Mayer | 73/38 |
| 6,119,506 A | 9/2000 | Gibson et al. | 73/38 |
| 6,358,570 B1 | 3/2002 | Affinito | 427/495 |
| 6,413,645 B1 | 7/2002 | Graff et al. | 428/446 |

FOREIGN PATENT DOCUMENTS

WO    WO00/42411    7/2000

* cited by examiner

Primary Examiner—Hezron Williams
Assistant Examiner—André K. Jackson
(74) Attorney, Agent, or Firm—Fitch, Even, Tabin & Flannery

(57) ABSTRACT

Method and apparatus for testing ultralow moisture permeation through a sample such as a thin barrier film by exposing one surface of a sample to be tested for moisture permeation to a predetermined humidity of HTO. The HTO permeating therethrough is collected in a stream of dry gas, preferably methane, at a known flow rate, and monitored for its radioactivity content. Monitoring over a period of time and appropriate conversion allows accurate assessment of even permeation rates measured as very low fractions of a gram of water per square meter per day.

9 Claims, 2 Drawing Sheets

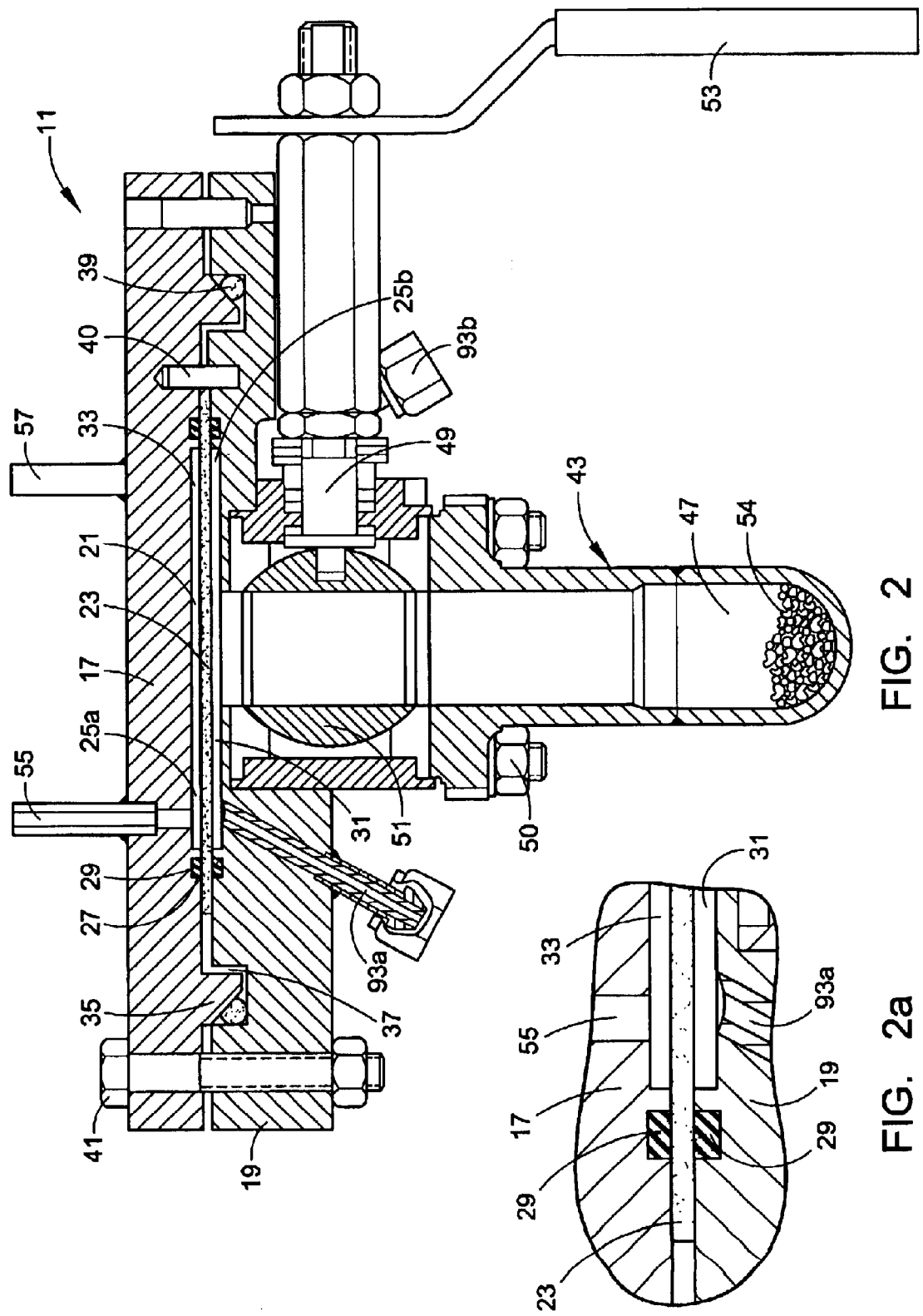

METHOD AND APPARATUS FOR MEASURING ULTRALOW WATER PERMEATION

The invention relates to methods and apparatus which allow the measurement of extremely low rates of permeation of water, and more particularly to methods and apparatus for measuring an ultralow moisture permeation rate through objects such as plastic films and the like.

BACKGROUND OF THE INVENTION

With the development of better and better barrier materials, generally from plastic films, it has become desirable to be able to precisely measure the rate of permeation through such barrier materials in order to properly evaluate them. As barrier materials have improved in their resistance to moisture permeation, it has become necessary to be able to accurately measure lower and lower rates of permeation.

Gas permeability measuring devices have generally been known in the art, and some of these have been directed to serve the garment industry where fabrics that are highly resistant to water permeation are often desired. However, more recently, with the development of LCD's, LED's and OLED's, it has become important to develop barrier materials that have an extremely high resistance to moisture permeation and oxygen permeation. It has been shown scientifically that there is a relationship between the permeation of moisture and the permeation of oxygen through a barrier; the proportion is that, if there is a permeation of water equal to $1 \times 10^{-4}$ grams per unit time, for the same unit time, there will be a permeation of oxygen of about $1 \times 10^{-3}$. Accordingly by measuring the moisture permeation rate, an adequate assessment can be obtained for the resistance of a particular object, such as a barrier film, to the permeation of both moisture and oxygen.

Because many present day products have been found to be highly sensitive to oxygen and moisture, often resulting in significant deterioration of the product, there has been a recent emphasis on developing better barrier materials. Products in the electronics fields, such as OLED's and LCD's, and certain pharmaceuticals are among products for which it is most important to resist such deterioration. The barrier materials that have been developed to protect such materials generally include multilayer composites of plastic films and thin layer inorganic materials, and the search has gone on for providing increasingly better multilayer, thin film barrier materials for this purpose. For example U.S. Pat. No. 6,413,645 entitled "Ultrabarrier Substrates" describes the problem and the search for more permeation-resistant materials.

In order to be able to effectively evaluate the performance of these new materials, adequate test equipment is required for detecting moisture permeation at these extremely low levels. Efforts have been made to use the amount of change in weight of a suitable desiccant in a closed container where the object closing the container has its opposite face exposed to a humid atmosphere as a measure of moisture permeation; however, the accuracy of such an apparatus has been frequently called into question. U.S. Pat. No. 4,663,969, issued May 12, 1987, discloses apparatus for testing water vapor transmission which employs a heated water bath; a solution containing a solute is employed along with an electric conductivity measuring device to measure the change in concentration, which will be indicative of moisture permeation. However, it is felt that such an apparatus is not suitable to measure extremely low rates of moisture permeation. U.S. Pat. No. 6,119,506 discloses an apparatus that is designed to allow measurement of mass transport. The flux of water vapor through a film or other object being measured is calculated by measuring results for exposure to a dry gas atmosphere, to a water-saturated atmosphere, and to atmospheres of different relative humidities; with a computer program being used to determine transmission rate for the object being tested. Humidity probes are used to provide outlet signals that are indicative of the water vapor concentration in nitrogen streams that are being caused to flow through a cell where such testing is occurring. In addition to being somewhat complicated, the apparatus is not felt to be well-suited to measuring extremely low moisture diffusion rates.

As a result, more accurate apparatus and methods have been sought for measurement of such ultralow permeation rates.

SUMMARY OF THE INVENTION

It has now been found that an apparatus for measuring ultralow water permeation through an object, such as a thin film, can be effectively created by utilizing tritiated water vapor (HTO). By suitably mounting the object to provide controlled access to opposite surfaces and by supplying tritiated water vapor to the upstream surface, vapor at the downstream surface can be collected and monitored to precisely determine even extremely low permeation rates through the object. The method particularly lends itself to execution by carefully controlling the humidity at the upstream surface and by creating a controlled flow of dry gas, such as nitrogen or methane, past the downstream surface. The flowing stream will collect the radioactive permeated HTO, and by causing it to flow past a radiation monitor, the moisture permeation rate can be quickly and accurately calculated.

BRIEF DESCRIPTION OF THE DRAWINGS

FIG. 2 is a sectional view through the mounting device shown in FIG. 1; and

FIG. 2a is an enlarged view of a portion of the device of FIG. 2.

DETAILED DESCRIPTION OF THE PREFERRED EMBODIMENT

Figure 1:
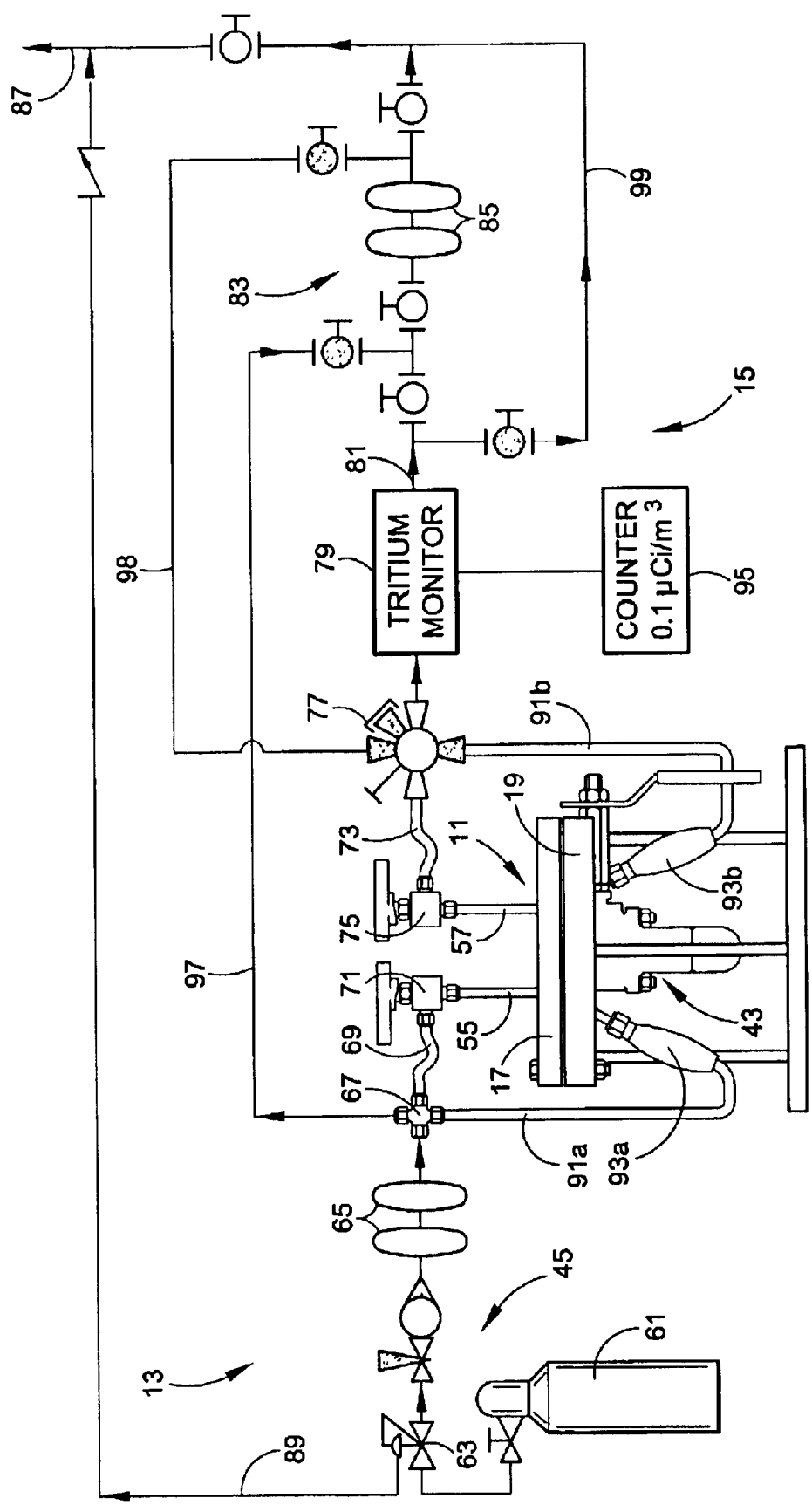
FIG. 1 is a schematic drawing showing apparatus for measuring ultralow water permeation through a thin film, which apparatus embodies various features of the invention.

The invention provides a method and apparatus for accurately measuring ultralow moisture permeation through an object, such as a thin film having a high resistance to moisture penetration. As earlier mentioned, there has been substantial development of new materials which provide high moisture and oxygen resistance for use as barriers for LCD's, LED's and OLED's which require such barrier protection to assure long term performance, particularly for the cathode components thereof, which are frequently manufactured of calcium and are particularly susceptible to degradation from moisture.

The apparatus shown in FIG. 1 includes a central mounting device 11 where the object for which the permeation of moisture is to be measured is appropriately mounted so that a precise surface area of it, at opposite upstream and downstream surfaces thereof, will be exposed so as to facilitate monitoring moisture permeation therethrough. Although the device 11 is designed to mount and measure permeation through a thin film, it can be understood that similar mounting devices would be constructed to handle objects of different shape and/or thickness.

Associated with the mounting device 11 is a system 13 for supplying controlled atmospheres to the upstream and to the downstream surfaces of the object being measured, and a system 15 for both monitoring the radioactivity of a gaseous stream exiting the device 11 and interpreting the information to calculate the moisture permeation rate through the object.

The illustrated mounting device 11 includes upper and lower halves or parts 17, 19. These two parts interface with each other to provide a central receptacle or chamber 21, which in the illustrated device is a shallow circular region designed to centrally mount a flat thin sample 23, the moisture permeation of which is to be determined. Accordingly, the central receptacle 21 is formed by a pair of facing shallow circular cavities 25a, 25b provided in the under surface of the upper part 17 and the top surface of the lower part 19. Surrounding each of these cavities is a circular groove 27 of preferably rectangular or square cross section, which groove accommodates a sealing ring 29 of resilient material that extends outward past the respective surface. Preferably sealing- or O-ring 29 of square or rectangular cross section are placed in each of these grooves 27 so that, when the upper and lower parts 17, 19 are clamped or otherwise pressed together, the O-rings 29 seal against a thin film object 23 the permeation of which is to be measured. As a result, the flat film then essentially splits the central receptacle 21 horizontally into a lower upstream subchamber 31 and an upper downstream subchamber 33.

To align the upper and lower parts 17, 19 of the mounting device, one of the parts is provided with a protrusion and the opposite part is provided with a complementary receptacle to receive the protrusion. In the illustrated embodiment, the upper part 17 is provided with a circular ridge 35 which is received in a circular groove 37 provided in the upper face of the lower part 19. The ridge 35 is preferably chamfered so as to accommodate an O-ring 39 to assure a tight fit and seal is obtained between the two halves once they are aligned as shown in FIG. 2. One or more locator pins 40 may also be provided. The halves are pressed tightly together by the employment of a number of carriage bolts and nuts 41, which bolts are received in a plurality of vertical passageways located about the periphery of the mounting device 11. Other suitable methods of pressing or clamping the two halves together so that the sample 23 being tested is sealed between the facing O-rings 29 could alternatively be used.

The gas supply system 13 includes a subsystem 4 for supplying an HTO atmosphere to the upstream subchamber 31 and a vapor collection subsystem 45 that includes an arrangement for supplying a flow of dry gas through the downstream subchamber 33 to collect the HTO that permeates through the sample 23 being tested.

The HTO supply subsystem 43 includes an HTO reservoir 47 connected through a ball valve 49 to the upstream subchamber 31 that is formed in the lower half 19 of the mounting device. The ball valve 49 is bolted or otherwise suitably secured to the lower half, and the HTO reservoir 47 is connected, as by bolts 50, in turn to the ball valve. The ball valve 49 includes the usual spherical valve member 51 and a handle 53 for rotating the spherical ball member 90 degrees from the open position shown in FIG. 2 to the closed position where communication between the HTO reservoir 47 and the upstream subchamber 31 is totally broken.

Any suitable source of HTO can be placed in the reservoir 47 before it is installed on the mounting device. Preferably, a crystalline salt 54 that forms a compound containing water of crystallization is used; more preferably, one that has a vapor pressure at ambient temperature which will provide a desired water partial pressure in the closed chamber comprising the reservoir, ball valve and upstream subchamber 31 is employed. Potassium chloride (KCl) is preferred, and anhydrous potassium chloride will form KCL.2HTO when exposed to HTO. For example, 0.8 g KCl and 1 cc of HTO will provide such a crystalline supply of HTO that will likely provide sufficient HTO for test purposes for as long as one year under normal test conditions and usage.

The upper part of 17 of the mounting device 11 contains a gas flow inlet passageway 55 leading into the upper subchamber 33 and a gas exit passageway 57 leaving an opposite region of the downstream subchamber. It is of course understood that the size of the mounting device and the subchambers can be varied as desired; however, it has been found that using a device that exposes about 100 sq. cm of a thin film sample 23 to a controlled atmosphere provides satisfactory test results and sufficient surface area so as to provide a representative test reading for thin film material designed to serve as barrier layers as well known in this art.

The overall gas supply system 13 includes a tank 61 of gas under pressure and the usual pressure regulator 63 to supply the gas to the mounting device at the appropriate pressure. Although various dry gases might be used, including argon, nitrogen and dry air, it has been found that methane is preferred because the molecular weight of methane is very close to the molecular weight of water, as a result of which any potential stratification in the downstream subchamber at low flow of gas therethrough is positively avoided. A test device such as this utilizing HTO, for general safety considerations, would normally be operated under a standard laboratory hood, and if methane is employed, the tank would normally also be located under the hood. If desired, a second cylinder of argon or the like might be also provided, with a 2-way valve to allow selection of either one for a particular test.

For example, ultradry methane at a tank pressure of 2500 psi may be fed through the pressure regulator 63 to reduce its pressure, to a suitable pressure for the testing/monitoring purposes of this invention. It is preferably passed first through a desiccant dryer 65 to remove any possible moisture that might be present.

The flow of methane leaving the desiccant dryer 65 enters a 4-way crossover connector 67 with one leg 69 leading through a small ball valve 71 to the gas inlet passageway 55. A similar exit conduit 73 containing a ball valve 75 is connected to the gas exit passageway 57 and leads to a 4-way connector 77 that contains a ball valve, which ball valve always allows flow out of the 4-way connector as depicted in FIG. 1 by the arrowhead, with rotation of the valve connecting the exit to one of 3 inlets for purposes to be explained hereinafter. During normal testing, the inlet stream from conduit 73 is directed through the valve. Both of the ball valves 71, 75 are connected to the 4-way connectors by flexible tubing so as to allow the upper part 17 of the mounting device 11 to be removed to facilitate the removal and replacement of the sample film 23 being tested, as explained hereinafter.

Normally, the ball valve connector 77 will allow flow from the exit conduit 73 horizontally straight through to a monitoring chamber 79, which is a commercial piece of equipment that is associated with a tritium monitor for monitoring the amount of radioactivity present in the permeated tritium, which emits beta particles. An outlet 81 from the radiation monitoring chamber 79 passes through a conduit network 83 that includes a desiccant dryer 85 which will remove and accumulate all HTO that was collected in the flow through the mounting device 11. Then the methane, stripped of all its radioactivity in the desiccant dryer 85, is vented through a suitable vent line 87. The overall gas supply network 13 also includes a second conduit 89 leading from the pressure regulator 63 to the vent line 87 through a check valve which serves as a safety bypass should, for some unknown reason, undesired high pressure reach the downstream side of regulator.

Lower conduits 91a and 91b lead from the first crossover 67 and to the second crossover 77, respectively. They are connected to a pair of ports 93a, 93b that connect to the upstream subchamber 31. These are provided for purging the upstream subchamber of any residual HTO preparatory to changing the sample 23 that is to be tested. To prepare to change the sample film, the ball valve 49 is closed, and then a purge flow of gas is caused to sequentially flow through the upstream and downstream subchambers until the radiation monitor 79 indicates there is no longer any radioactivity present in either of these two gas streams that are exiting from the mounting device. When the ball valve connector 77 is rotated generally counterclockwise, as depicted, the methane flow from the pressure regulator 63 becomes a purge flow through the conduits 91a, b and the upstream subchamber 31. Preferably after the radiation monitor 79 indicates the upstream chamber 31 has been purged, the downstream chamber 33 is purged.

In addition, the conduit network 83 includes a bypass conduit 79 incorporating a suitable valve which allows a purge flow of dry gas to be directed through the network downstream of the radiation chamber 79 through the dryer 85, and then back through the radiation chamber; such flow pattern may be used generally before replacement of conduits or components is undertaken in this region to assure that there is no residual radioactivity in the system itself or to ascertain that the dryer 85 is effectively sequestering all of the HTO. By rotating the valve in the connector 77 clockwise, as depicted in FIG. 1. a side flow conduit 98 containing a suitable off/on valve is interconnected to the exit so as to route the flow exiting the dryer 85 back to the tritium monitor 79. By opening a valve in a second bypass conduit 99, this flow path of dry gas from the conduit 97 to the vent 87 via sequential flow through the dryer 85 and then through the radiation monitor 79, is completed.

The radiation monitor 79 is connected to a conversion unit 95 which can include a CPU that is programmed to make calculations from the signals received from the radioactivity monitor to determine the amount of HTO collected during a given period of time for a known flow of methane gas. From such readings and the knowledge of the amount of liters of gas flow and the length of time during which the test was carried out, the unit 95 is programmed to provide a readout in the form of the number of grams of water, i.e. HTO, which permeate through the sample 23 being tested, per square meter per day (or other desired unit of time) under ambient conditions.

As an example of the overall operation, an appropriate sized sample 23 of a barrier film to be tested is carefully installed in the mounting device 11 so that it rests upon the upper surface of the protruding square cross-section O-ring 29 in the lower half 19 of the device, as best seen in FIG. 2a. The upper half 17 is then carefully set in place, and the carriage bolts and nuts 41 installed so as to clamp the film 23 securely between the mating O-rings 29 and to seal the central receptacle about its periphery by the O-ring 39. The ball valve 49 is then opened so as to allow the upstream subchamber 31 to be filled with an HTO partial pressure at the surface of the sample 23 being tested. Generally, after the sample 23 is installed, a period of about an hour is allowed to pass to permit the HTO to generally saturate the film sample. During this time, a slow flow of dry methane is allowed to pass through the downstream subchamber 33 until it is noticed that some radiation is being detected. After a further short period of time, a timer in the conversion unit 95 is activated, and the actual test begun with a standard flow of methane, for example, about 1 liter per hour of dry methane, being caused to flow through the downstream subchamber 33 and then through the radiation monitor 79. If desired a volumetric flow monitor (not shown) may be included to assure precision; however, such should not be necessary, as small variations can be tolerated. As previously indicated, the methane/HTO leaving the radiation monitor 79 passes through the final desiccant dryer 85, which absorbs all the collected HTO exiting the radiation monitor and allows only totally dry, non-radioactive methane to flow out the vent 87. The signals generated at the radiation monitor 79 for the time of the test are continuously fed to the conversion unit 95 which is programmed to calculate a moisture permeation rate in desired terms, as for example, grams of water per square meter of surface area per day.

As previously mentioned, when the test has been satisfactorily completed, the ball valve 49 is closed, and the upper and lower subchambers 33, 31 are totally purged of HTO by flowing dry methane through both chambers until no radiation is still being detected. Then the mounting device 11 is opened, and the sample 23 is removed and replaced with the next one to be tested.

Although the invention has been described with regard to certain preferred embodiments which constitute the best mode presently known to the inventors to carry out the invention, it should be understood that various changes and modifications as would be obvious to one having ordinary skill in this art can be made without departing from the scope of the invention which is defined by the claims that are appended hereto. Even though the working example is directed to testing improved barrier materials suitable for the formation of a flexible OLED or the like, it should be understood that other materials may alternatively be tested by appropriately altering the mounting device. Disclosures of all previously enumerated U.S. patents are expressly incorporated herein by reference. Particular features of the invention are enumerated in the claims appended hereto.

What is claimed is:

1. Apparatus for measuring ultralow water permeation through a film via the safe use of tritiated water vapor (HTO), which apparatus comprises:

means for mounting the film through which permeation of water is to be measured to provide controlled access to a first chamber at an upstream surface and a second chamber at a downstream surface thereof, means for supplying tritiated water vapor (HTO) to the first chamber and to the upstream surface of the film, means for circulating a flow of carrier gas through the second chamber to provide a stream containing HTO permeating from the downstream surface of the film, conduit means for flowing said stream from said second chamber to a radiation monitor for continuously monitoring said stream for radioactivity and creating signals indicative of radioactivity, conversion means for receiving signals from said radiation monitor and converting the signals to calculate the water permeation rate through the film at that moment, a conduit network which leads from said radiation monitor to a vent to exhaust the carrier gas, a station for removing all HTO from the carrier gas stream flowing in said network following exit of the carrier gas stream from said radiation monitor and for accumulating said removed HTO, means for segregating said HTO supplying means from communication with said first chamber following testing of a sample film, and means for purging said first chamber with gas to remove all HTO therefrom and for directing said purge gas into said conduit network and to said radiation monitor prior to travel to said station for removal of HTO prior to venting of said purge gas, which arrangement provides an indication when said first chamber has been purged of all HTO.

2. The apparatus for measuring ultralow water permeation according to claim 1 wherein said segregating means is a ball valve.

3. A safe method for measuring ultralow water permeation through a film using tritiated water vapor, which method comprises the steps of:

mounting the film through which permeation of water is to be measured to provide controlled access to an upstream surface in a first chamber and to a downstream surface in a second chamber, supplying tritiated water vapor (HTO) from a source to the upstream surface of the film in the first chamber, collecting HTO permeating from the downstream surface of the film by circulating a flow of dry carrier gas through the second chamber to provide a stream containing permeated HTO, flowing said stream from said second chamber to an entrance to a third chamber containing a radiation monitor, continuously monitoring said stream for radioactivity and generating signals, receiving signals from said radiation monitor in conversion means and converting the signals to calculate the water permeation rate through the film at that moment, exhausting the carrier gas stream exiting said third chamber through a conduit network which contains an HTO removal station and leads to a vent, removing all HTO from the carrier gas stream flowing in said network following its exit from said third chamber and accumulating said removed HTO in the station, periodically segregating the HTO source from communication with said first chamber following testing of a sample film, purging the first chamber with gas to remove all HTO therefrom, and directing said purge gas through said conduit network so as to remove all HTO purged from the first chamber prior to venting of said purge gas.

4. The method for measuring ultralow water permeation according to claim 3 which further includes directing said purge gas stream from the first chamber to said third chamber containing the radiation monitor to provide an indication when said first chamber has been purged of all HTO.

5. The method for measuring ultralow water permeation according to claim 4 which includes the step, following said purging of all HTO from the first chamber, of flowing purge gas through said second chamber to purge it of all residual HTO.

6. The method for measuring ultralow water permeation according to claim 3 wherein said conduit network includes a bypass conduit connected to said gas purging means, which method further includes the step of flowing purge gas through the network at a location downstream of the third chamber, then through said HTO removal station, then through a side conduit leading to the entrance to the third chamber, and then to the vent to ascertain that the conduit network is purged of residual HTO.

7. The method for measuring ultralow water permeation according to claim 3 wherein said carrier gas is dry methane.

8. Apparatus for measuring ultralow water permeation through a film via the safe use of tritiated water vapor (HTO), which apparatus comprises:

means for mounting the film through which permeation of water is to be measured to provide controlled access to a first chamber at an upstream surface and a second chamber at a downstream surface thereof, means for supplying tritiated water vapor (HTO) to the first chamber and to the upstream surface of the film, means for circulating a flow of carrier gas through the second chamber to provide a stream containing HTO permeating from the downstream surface of the film, conduit means for flowing said stream from said second chamber to a radiation monitor for continuously monitoring said stream for radioactivity and creating signals indicative of radioactivity, conversion means for receiving signals from said radiation monitor and converting the signals to calculate the water permeation rate through the film at that moment, a conduit network which leads from said radiation monitor to a vent to exhaust the carrier gas, a station for removing all HTO from the carrier gas stream flowing in said network following exit of the carrier gas stream from said radiation monitor and for accumulating said removed HTO, means for segregating said HTO supplying means from communication with said first chamber following testing of a sample film, and means for purging said first chamber with gas to remove all HTO therefrom and for directing said purge gas into said conduit network and said station for removal of HTO prior to venting of said purge gas, said conduit network including a bypass conduit connected to said gas purging means which allows a flow of purge gas to be directed through said network at a location downstream of the radiation monitor so as to flow through said HTO removal station, then to said radiation monitor, and then to the vent in order to ascertain that the conduit network is purged of residual HTO.

9. The apparatus for measuring ultralow water permeation according to claim 8 wherein said segregating means is a ball valve.

* * * * *